USOO5576015A

United States Patent [19]
Donzis

[11] Patent Number: 5,576,015
[45] Date of Patent: Nov. 19, 1996

[54] SUBSTANTIALLY PURIFIED BETA (1,3) FINELY GROUND YEAST CELL WALL GLUCAN COMPOSITION WITH DERMATOLOGICAL AND NUTRITIONAL USES

[76] Inventor: Byron A. Donzis, #18 W. Rivercrest, Houston, Tex. 77042

[21] Appl. No.: 396,490

[22] Filed: Mar. 2, 1995

[51] Int. Cl.$^6$ .......................... A23K 1/165; A23K 1/17; A61K 31/715; A23L 1/30

[52] U.S. Cl. ...................... 424/442; 514/54; 426/648

[58] Field of Search ........................ 514/54; 424/442; 426/648

[56] References Cited

U.S. PATENT DOCUMENTS

| | | | |
|---|---|---|---|
| 3,943,247 | 3/1976 | Komatzu et al. | 514/25 |
| 4,072,567 | 2/1978 | Yokobayashi et al. | 435/72 |
| 4,343,784 | 8/1982 | Massot et al. | 424/45 |
| 4,705,780 | 11/1987 | Massot et al. | 514/54 |
| 4,739,046 | 4/1988 | DiLuzio | 536/117 |
| 4,761,402 | 8/1988 | Williams et al. | 514/54 |
| 4,769,363 | 9/1988 | Misaki et al. | 514/54 |
| 4,818,752 | 4/1989 | Williams et al. | 514/54 |
| 4,833,131 | 5/1989 | Williams et al. | 514/54 |
| 4,962,094 | 10/1990 | Jamas et al. | 514/54 |
| 4,992,540 | 2/1991 | Jamas et al. | 536/123 |
| 5,032,401 | 7/1991 | Jamas et al. | 424/426 |
| 5,223,491 | 6/1993 | Donzis | 514/54 |

FOREIGN PATENT DOCUMENTS 63-83012  4/1988  Japan.

OTHER PUBLICATIONS

"Promotion of Wound Repair in Mice by Application of Glucan", Leibovoch, S. A. and Danon, Journal of the Reticuloendothelial, Sec 27:1–11 (1980.

"Promotion of Wound Healing by Yeast Glucan Evaluated On Single Animals"—Wolk, M. and Danon, D. Medical Biology 63:73–80 (1985).

"Dynamica of Blood Components and Peritoneal Fluid During Treatment of Murine *E. coli* Sepsis with β–1, 3–D–polyglucose Derivatives", Rasmussen, L. T., Fandrem, Jr., and Seljelid, R. Scand. J. Immunol. 32, 333–340 (1990).

"MacroGard-S—A New Concept For Feeding Starter Pigs", Dr. W. D. Schoenherr Dr. D. S. Pollmann, & Dr. J. A. Coalson. A Report From Research, No. H–102, Oct. 1993.

"CM–Glucan a New Yeast Polysaccharide For Cosmetic Use", Dr. Fred Zulli & Christine Saecher, Mibelle AG Cosmetics, Bolimattstr I, 5033 Buchs, SW.

"The Mollecular Constitution of an Insoluble Polysaccharide From Yeast *Saccharomyces cerevisae*", Hassid, W. Z., Joslyn, M. A. and McReady, R. M., Journal of American Chemical Society, 63:295–298 (1941).

"Effect of Orally Administered β–Glucan on Macrophage Function in Mice", Suzuki, Iwao, Tanaka, Hideki, Konoshita, Akira, Oikawa, Shozo, Osawa, Masumi and Yadomae, Toshiro. Journal of Immunopharmac, vol. 12, No. 6, pp. 675–684, (1990).

"Novel Immunomodulators With Pronounced In Vivo Effects Caused by Stimulation of Cytokine Release", Rasmussen, L. T. and Seljelid, R., Journal of Cellular Biochemistry 46:60–68 (1991).

"Heterogeneity of Glucan Preparations From The Walls of Various Yeasts" Manners, D. J., Masson, A. J. & Patterson, J. C. J. of Gen Micro. 411–417 (1974).

"Mixed–linked β–(1→3), (1→4)–D–glucans in the Cell Walls of Barley and Oats—Chemistry and Nutrition", Aman, Per and Graham, Hadden, pp. 41–51.

Westlaw Search Report.

*Primary Examiner*—Carlos Azpuru
*Attorney, Agent, or Firm*—Sue Z. Shaper; Butler & Binion, L.L.P.

[57] ABSTRACT

Substantially purified beta (1,3) glucan extracts obtained from yeast cell walls, particularly finely ground, and including nutritional and dermatological applications, are disclosed.

13 Claims, 3 Drawing Sheets

SUBSTANTIALLY PURIFIED BETA (1,3) FINELY GROUND YEAST CELL WALL GLUCAN COMPOSITION WITH DERMATOLOGICAL AND NUTRITIONAL USES

BACKGROUND OF INVENTION

1. Field of Invention

The present invention is related to nutritional and dermatological uses of yeast glucans.

2. Description of Related Art

Glucans are polymers of glucose. Such glucans may be derived from the cell walls of yeast. Yeast glucans containing beta (1,3)-linked glucopyranose backbones have been known to have biological activity. Specifically they have been shown to activate the immune system across kingdom lines.

Glucan extracted from yeast cell walls is known to be a potent stimulator of the immune system. Studies have indicated that parenteral administration of glucan significantly modifies host resistance to a wide variety of infectious disease induced by bacterial, fungal, viral, and parasitic organisms (DeLuzio, *Trends in Pharmacological Science*, 4:344–347, 1983). Glucan has also been shown to have potent antitumor activity (DeLuzio et al., *Advances and Experimental Medicine and Biology*, 21A:269–290, 1979). The mechanism by which glucan exerts its beneficial effects is believed to be by interaction with specific glucan receptors located on the macrophage cells. (Czop, *Pathology & Immunopathology Res.*, 5:286–296, 1986). The above studies teach, however, a toxic effect from the parenteral administration of yeast extract beta (1–3) glucan that appears to render the product unusable. This toxic effect is believed to derive from the particulate nature of the product, and has lead to a search for an effective water soluble yeast glucan extract.

The general method for the production of glucan from yeast involves extraction with alkali followed by extraction with acid (Hassid et all, *Journal of the American Chemical Society*, 63:295–298, 1941). Improved methods for isolating a purified water insoluble beta (1,3) glucan extract are disclosed in this inventor's earlier patent, U.S. Pat. No. 5,223,491 ("'491 patent"), which is incorporated herein by reference in its entirety.

The '491 patent further discloses the use of yeast extract beta (1,3) glucans as dermatological agents. Because of its insolubility in water, however, the glucans taught in the '491 tend to fall out of suspension in dermatological formulations, reducing the effectiveness of such formulation and rendering such formulations aesthetically undesirable. It would therefore be desirable to have an improved beta (1,3) glucan topical formulation more suitable for dermatological use, in particular one comprising a substantially purified beta (1,3) glucan that will not fall out of suspension prior to use. It would be further desirable to have a beta (1,3) glucan product that is useful as a nutritional supplement in a broad spectrum of animals, from crustaceans to humans.

SUMMARY OF THE INVENTION

The present invention is related to the use of purified beta (1,3) yeast extract glucan particles, in particular finely ground, as nutritional supplements and as dermatological agents.

DETAILED DESCRIPTION OF THE PREFERRED EMBODIMENT(S)

Figure 1:
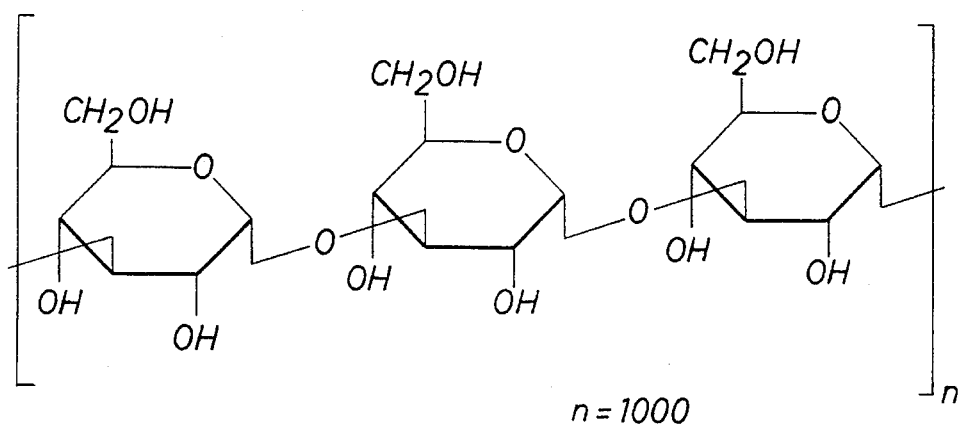
FIG. 1 illustrates the yeast cell wall comprising predominantly beta(1,3)glycosidic linkages.

The present invention is directed to substantially purified, beta (1,3) yeast extract glucans, in particular glucans having a fine particle size, which are useful in both dermatological and nutritional applications. As used herein, the term "substantially purified beta (1,3) yeast extract glucan" refers to a yeast cell wall extract comprising predominantly beta (1,3) glycosidic linkages, as illustrated in FIG. 1.

Figure 2:
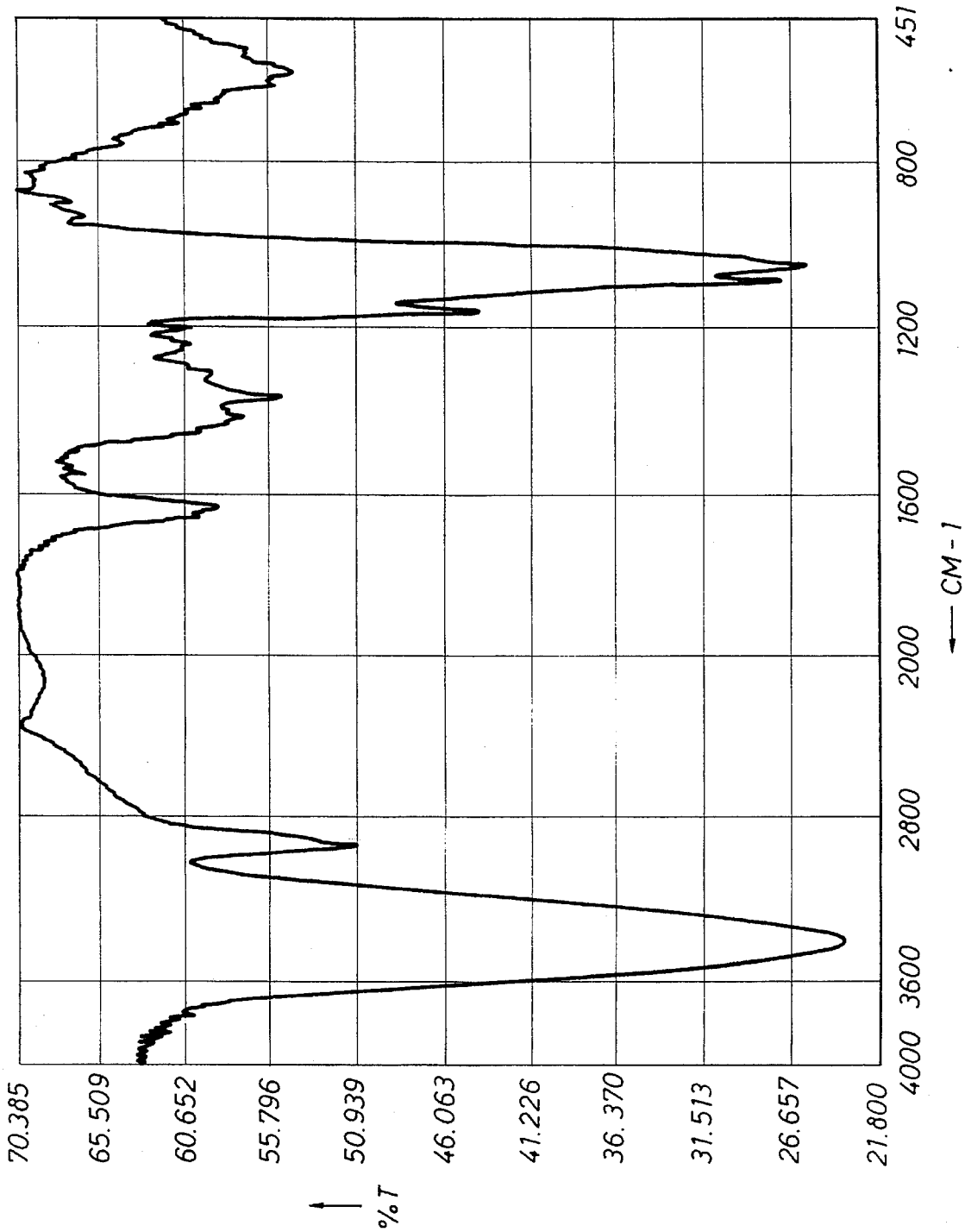
FIG. 2 illustrates an FTIR spectrum of beta(1,3)glucan isolated from yeast cell walls.

The Fine Grind Beta (1,3) Glucan:

The beta (1,3) glucan may be isolated from yeast cell walls by conventional methods known by those of ordinary skill in the art, including the method disclosed in the '491 patent discussed herein. FIG. 2 illustrates an FTIR spectrum of such beta glucan. An improved glucan product is obtained when the average particle size is preferably about 1.0 microns or less, and more preferably about 0.20 microns or less.

To obtain the desired smaller particle size, the mixture comprising the beta (1,3) glucan product is ground down using a blender or ball mill, for example. One preferred grinding or particle size reduction method utilizes a blender having blunt blades, wherein the glucan mixture is blended for a sufficient amount of time, preferably several minutes, to completely grind the particles to the desired size without overheating the mixture. Another preferred grinding method comprises grinding the glucan mixture in a ball mill with 10 mm stainless steel grinding balls. This latter grinding method is particularly preferred when a particle size of about 0.20 microns or less is desired.

Prior to grinding, the glucan mixture is preferably passed through a series of sieves, each successive sieve having a smaller mesh size than the former, with the final mesh size being about 80. The purpose of sieving the mixture is to separate the much larger and more course glucan particles from smaller particles (the pore size of an 80 mesh sieve is about 0.007 inches or 0.178 mm). The separated larger particles are then ground down as described above and re-sieved to a final mesh size of 80. The process of sieving and grinding is repeated until a final mesh size of 80 is obtained. The sieved particles are combined and ground down further, preferably for at least an hour, until the desired particle size is obtained, preferably about 1.0 micron or less, more preferably about 0.20 microns or less. Periodic samples of the fine grind glucan are taken during the grinding process and measured using a micrometer on a microscope.

Nutritional Supplementation:

Both the fine grind and non-ground substantially purified beta (1,3) glucan, more preferably the fine grind glucan described herein, may be administered orally. Finely ground glucan may be administered parenterally. It is believed that upon oral administration, the smaller or finer particle sized glucan is more quickly dissolved in the gastrointestinal tract, and consequently more readily absorbed, as compared to a non-ground glucan product which comprises larger sized glucan particles. Toxic effects have not been detected. It is believed that a fine grind glucan is even more systemically effective than a soluble version. The preferred particle size of the find grind glucan product is about 1.0 micron or less, and more preferably, 0.20 microns or less. Preferred amounts of glucan product administered for nutritional purposes, to enhance growth and survival, have been, orally from about 0.20 mg to about 1.0 mg per 1.0 kg of animal body weight and, parenterally, from about 0.001 mg to about 0.3 mg per gram of body weight.

Both the fine grind and the non-ground substantially purified beta (1,3) glucan product may be administered to animals as a significant nutritional supplement for the purpose of improving both growth and survival in these animals, as well as enhancing growth rate and feed efficiency. Suitable animals include, but are not limited to, fish, crustaceans, domestic farm animals such as pigs, poultry, horses, sheep, and cattle, for example, as well as fowl and humans. The glucan's mechanism of action as a useful nutritional supplement is believed to be via the activation of macrophages, thereby improving the animal's immune system. By enhancing the animal's general resistance to diseases, both viral and bacterial, growth and survival rates can be significantly improved.

Dermatological Applications:

The inventive fine grind beta (1,3) glucan may be combined with a suitable pharmaceutical carrier for topical application to the skin. Carrier compositions suitable for topical application to the skin would include, for example, creams, lotions, and ointments and the excipients typically used therein. Dermatological preparations comprising the inventive fine grind water-insoluble glucan, and the various methods for using these dermatological preparations are the same as described in the '491 patent which is incorporated herein by reference in its entirety, as discussed above.

In topical preparations, it is believed that the smaller particle sized glucans are more efficacious as dermatological agents. It is also believed that particle size plays a role in allowing the fine grind glucan particles to stay better suspended in the base carrier, such as glycerine, for example, thereby making the glucan particles less likely to fall out of suspension prior to use.

As described in the '491 patent, the amount of water-insoluble glucan to be used and the specific components of the particular composition will depend upon the nature of the product and its intended use. Generally, the effective amount of glucan will preferably range from about 0.001 w/w % to about 10 w/w % of the composition, more preferably from about 0.1 w/w % to about 4 w/w %. Some preferred concentration ranges for particular pharmaceutical formulations/uses are as follows: body lotions and creams: 1–2%; skin care creams and gels: 2–7%; eye care products: 1–5%; concentrated products (creams, serums, unidoses, etc.): up to 10%; as a co-active agent: 1–7%; and decorative cosmetics (powder form): 0.001–0.015%. As with many dermatological products, the product is preferably stored in a cool place (+5° C.) for a maximum of one month after first use and the container should be shaken to optimize homogeneity.

A particularly useful dermatological formulation of the fine-grind glucan product further comprises glycerine and a surfactant, most preferably a glycol selected from the group consisting of 1,3-butylene glycol and propylene glycol, more preferably 1,3-butylene glycol. When used in dermatological preparations, a preservative should also be added. A particularly useful preservative for cosmetic applications which is preferred in the present composition is marketed under the trademark PHENONIP by NIPA Laboratories of Wilmington, Del. [PHENONIP comprises methyl paraben (15.0–17.0 w/w %), ethylparaben (3.5–4.5 w/w %), n-propylparaben (1.6–2.4 w/w %), iso-butylparaben (1.6–2.4 w/w %), n-butylparaben (3.5–4.5 w/w %), mixed alkyl esters of p-hydroxybenzoate (27.0–28.3 w/w %), and 2-phenoxyethanol (71.7–73.0 w/w %)]. While PHENONIP is the most preferred preservative in the present topical formulation, other preservatives typically known by those of ordinary skill in the art, especially those preservatives which are particularly useful in cosmetic formulations, may be employed.

The foregoing ingredients are then blended at maximum speed for a time period ranging from about 15 to about 30 minutes, more preferably about 20 minutes, until the finely ground glucan is evenly dispersed. Preferably a blender or high shear mixer is used to blend the ingredients. This beta (1,3) glucan topical preparation, hereinafter referred to as the "glycerine formulation", may be stored in sterile bottles at room temperature for future use as a topical dermatological agent or for use in other topical dermatological preparations, for example.

Preferably, the glycerine formulation comprises from about 0.01 w/w % to about 5 w/w %, more preferably about 0.1 w/w %., of the finely ground glucan extract; from about 10 w/w % to about 50 w/w %, more preferably from about 30.4 w/w % of glycol (most preferably 1,3-butylene glycol), and from about 50 w/w % to about 90 w/w %, more preferably about 69 w/w % of glycerine. Preferably, from about 0.30 w/w % to about 0.50 w/w % of a preservative, more preferably about 0.50 w/w %, is also included in the glycerine preparation.

The inventive beta (1,3) glucan extracts, preferably the fine grind glucan, when combined with a suitable carrier, preferably glycerine as described for the glycerine formulation, are particularly useful in reducing skin erythema, skin roughness, pigmentation, and irritation resulting from some type of insult to the skin, such as UV radiation. The inventive glucan extracts described herein are also useful as photoprotective agents and reduce the erythema associated with overexposure to the sun.

The following examples do not limit the scope of the invention, but are intended to illustrate the various aspects of the invention.

EXAMPLE 1

Preparation of Ground Yeast Glucan

A mixture of substantially purified beta (1,3) glucan isolated from yeast cell walls, prepared in accordance with methods known in the art, was placed in a blender having blunt blades. The particle size of the glucan mixture was significantly reduced by beating the mixture in the blender for several minutes. The resulting particle size of the mixture was reported as substantially colloidal, at least 1.0 microns or less.

EXAMPLE 2

Preparation of Fine Grind Yeast Glucan

A mixture of substantially purified beta (1,3) yeast cell wall glucan was passed through a series of sieves, with the final sieves having a mesh size of 80, to remove large chunks. The material smaller than 80 mesh was ground in a Brinkman ball mill, periodically tested and re-sieved to 80 mesh. 10 mm stainless steel balls were used in the ball mill to produce a particle size of about 0.20 microns or less. This particle size was confirmed using a micrometer on a microscope, sampling after one hour of milling and then approximately every 30 minutes thereafter until the desired size was achieved.

EXAMPLE 3

Oral Nutritional Efficacy of Yeast Glucan Product

The water-insoluble beta (1,3) glucan product of Example 1 was administered orally to mice to determine its oral nutritional efficacy. Three groups of mice, each group comprising 15 mice, were tested. Each animal in Group 1 (the control group) was administered PBS (i.e. physiologically buffered saline) every day for four days. Each animal in Group 2 was administered 1.0 mg/kg of the glucan daily for four days, and each animal in Group 3 was administered 0.20 mg/kg of the glucan for four days.

On each of the first three days, each animal received a dose of the appropriate test substance (i.e. PBS or the glucan). Twenty-four hours after each daily dose and on day seven of the testing period (i.e. about 168 hours after the first administration), three of the animals from each group were inoculated with a predetermined dose of *Staphylococcus aureus*. Twenty minutes following inoculation, the peritoneal cavity was washed, and the peritoneal exudate cells were collected. These cells were then examined microscopically to determine the percentage of cells which had phagocytized at least four bacteria.

Figure 3:
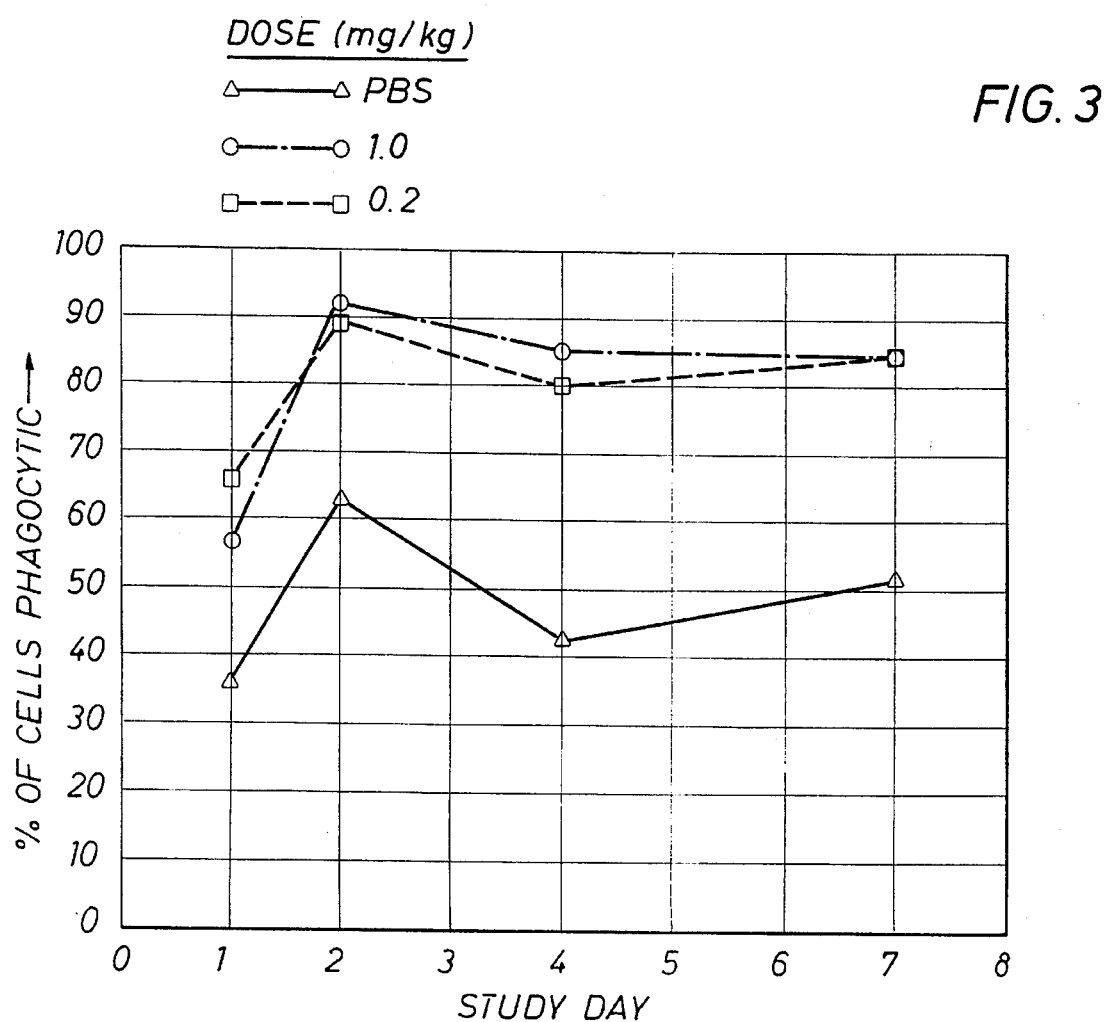
FIG. 3 illustrates that beta (1,3) glucan can strongly enhance bacterial phagocytosis peritoneal exudate cells, and is maintained by sequential oral dosing.

The results were expressed as the mean % of the three groups tested for each observation and are illustrated by the graph in FIG. 3. Phagocytic values were determined by the same observer for all observations except for Day 3. The Day 3 observer's results, while similar in relative terms, was not consistent in absolute terms with those of the primary observer, and were therefore excluded from the graphical analysis. The results of the study showed that:

(1) the beta (1,3) glucan can strongly enhance bacterial phagocytosis of *S. aureus* by peritoneal exudate cells (chiefly macrophages); and (2) enhancement of phagocytosis may be maintained by sequential oral dosing. Normally, after a single dose, phagocytic performance peaked at about 72 hours and then returned to control level by 144 hours (i.e. six days) following administration.

This demonstration of bacterial enhancement via oral dosing suggests application for the water-insoluble beta (1–3) yeast extract glucan as a component in a combined modality with conventional nutritional materials, including other anti-infective agents. Water-insoluble yeast glucan, through the stimulation of host defense systems, creates a more supportive environment within the body to assist the primary killing action of conventional agents and thereby to enhance significantly growth and survival.

EXAMPLE 4

Dermatological Activity of Fine Grind Glucan Product

A study was performed comparing the dermatological activity of the product prepared as described in Example 2 and formulated in a conventional pharmaceutical carrier (Nayad FG), a hydrocortisone preparation, a non-yeast derived (1,3) beta glucan, 10% aloe, and a non-treated control. The upper layer of skin (i.e the stratum corneum) was removed or stripped away on ten human subjects per agent/control to induce erythema. Subjects were treated twice a day beginning immediately after the initial skin stripping.

When left untreated, previously stripped skin generally heals by re-forming with a rough scaly texture and increased pigmentation. Reduction in skin erythema was measured using a Perimed 2PF laser Doppler velocimeter, and the results are shown in Table 1.

Skin roughness was measured by image analysis of Silflo replicas, and skin pigmentation was measured with the L value of the Minolta Meter, with decreases representing increased color. Results are shown in Table 2.

TABLE 1

REDUCTION IN SKIN ERYTHEMA

| Skin Treatment | Pre-treatment blood flow | 1 day after stripping | 3 days after stripping | 5 days after stripping |
|---|---|---|---|---|
| None (control) | 1.0 | 4.67 | 4.11 | 2.45 |
| 0.1% hydro-cortisone | 1.0 | 3.11 | 1.44 | 1.21 |
| 0.007% Nayad FG | 1.0 | 3.72 | 2.67 | 1.88 |
| 2% Oat 1,3 B glucan | 1.0 | 4.66 | 4.01 | 2.11 |
| 10% aloe | 1.0 | 4.40 | 3.78 | 2.78 |

TABLE 2

SKIN COLOR AND ROUGHNESS

| Skin Treatment | Pre-treatment skin roughness | Roughness 8 weeks after stripping | Increase in skin color 8 weeks after stripping |
|---|---|---|---|
| None (control) | 1.0 | 1.72 | −4.50 L units |
| 0.1% hydro-cortisone | 1.0 | 1.56 | −0.60 L units |
| 0.007% Nayad FG | 1.0 | 1.33 | −1.02 L units |
| 10% aloe | 1.0 | 1.67 | −3.22 L units |

EXAMPLE 5

The photoprotective effects of a glycerine topical preparation comprising 4 w/w % of the fine grind beta (1,3) glucan prepared according to the process described in Example 2 was compared to other agents. The Minimal Erythemal Dose (MED) was determined for each individual by administering a series of five doses of UVA and UVB (290–400 nm) to the test sites using a 150-watt Xenon solar stimulator, wherein each dose was 25% greater than the previous one. 24 hours after the UV irradiation, the sites were evaluated to determine the MED for each test subject. The MED was multiplied by the theoretical SPF of the test agents to determine the median irradiation time for each test agent. The MED for protected skin was determined by administering a series of five doses, each 25% greater than the previous one (two doses below the median and two doses above the median). The exposed sites were evaluated 24 hours after the UV irradiation for the MED for the protected skin. The SPF for each test agent was calculated by dividing the MED for protected skin by the MED for unprotected skin.

Numbered test sites were marked on the backs of each test subject. Approximately 3 mg/cm$^3$ of test agent was applied to the test sites as per Table 3 prior to irradiation (when called for). Erythema was graded visually and with a Minolta Chroma Meter at 1 hour and at 24 hours after UV exposure. Since very little erythema was developed at any of the sites at the one hour reading, only the readings obtained at the 24 hour reading were evaluated.

The data obtained using the Minolta Meter are shown in Table 4. With the Minolta Meter, a 10% reduction in erythema was observed when the 4% glycerine formulation in combination with an SPF 2 product was applied a single time prior to UV exposure. With five applications of this same formula, a 64% reduction in erythema was observed when both treated and untreated sites were exposed to a 2 MED dose of UV (sites 3 vs. 4).

Additionally, protection was observed when the UV dose was increased 25% (a 31% protection comparing 3 vs. 4A). When the UV dose was increased 50%, no protection was observed (sites 3 vs. 4B). When the 4% glycerine formulation was added to an SPF 15 product and a UV dose of 15 MED's was given, no protective effects were observed with a single application of the 4% glycerine formulation (sites 5, 6, 6A, and 6B).

Table 5 contains data obtained from the visual examination of the test sites upon application of the test agents. Erythema that was clearly visible was graded as a 1.0. If slight reddening of the site was observed, a grade of "+" was recorded. The addition of the 4% glycerine formulation to an SPF 2 product significantly increased the photoprotective nature of the product when the 4% glycerine formulation was applied 5 days prior to the UV exposure.

EXAMPLE 6

Parenteral Nutritional Efficacy of Glucan Product

Figure 4:
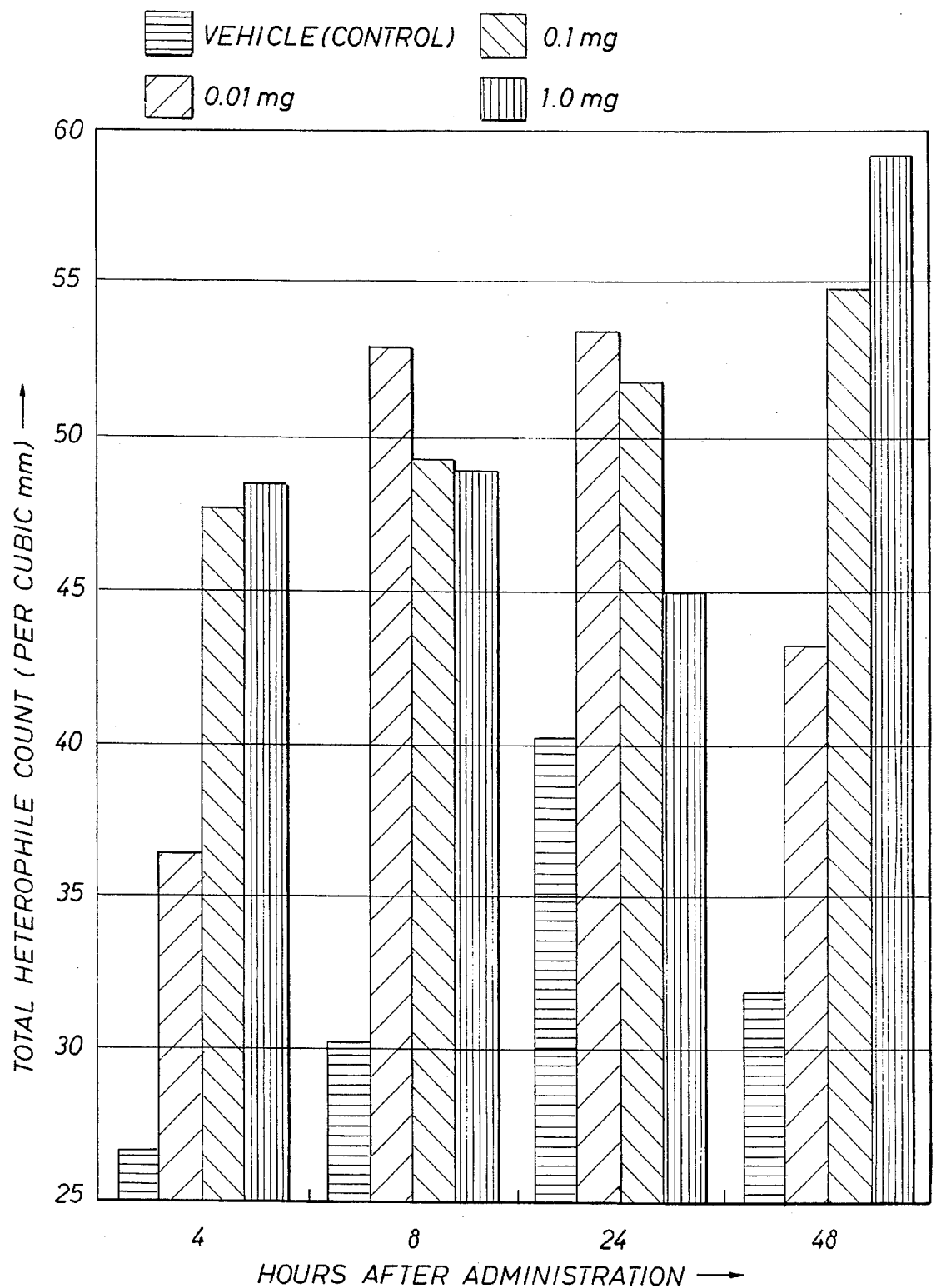
FIG. 4 illustrates that a mixture of purified beta (1,3) yeast cell wall glucan can strongly enhance the white cell count in day old chicks.

A product substantially prepared as described in Example 2 was parenterally administered to day old chick groups in a variety of dosage levels. Upon sacrifice at intervals of several hours, a heightened count of white cells was detected in the blood count in each instance in each administered group. Dosage levels ranged from 0.01 mg to 1.0 mg per day old chick, which average approximately 30 grams. See FIG. 4.

TABLE 3

| Site Number | Product/Treatment | UV Exposure |
| --- | --- | --- |
| 1 | no product | no UV |
| 2 | base lotion | UV 2.0 MED |
| 3 | base + 4% glucan* - 1 appl. before UV | UV 2.0 MED |
| 4 | base + 4% glucan* - 5 day appl. before UV | UV 2.0 MBD |
| 4A | base + 4% glucan* - 5 day appl. before UV | UV 2.0 MED plus 25% |
| 4B | base + 4% glucan* - 5 day appl. before UV | UV 2.0 MED plus 50% |
| 5 | SPF 15 - 1 appl. before UV | UV 15 MED |
| 6 | SPF + 4% glucan* - 1 appl. before UV | UV 15 MED |
| 6A | SPF + 4% glucan* - 1 appl. before UV | UV MED plus 25% |
| 6B | SPF + 4% glucan* - 1 appl. before UV | UV MED plus 50% |
| 10 | 4% glucan* after UV exposure | UV 2.0 MED |

*4% glucan = glycerine/1,3-butylene glycol composition comprising 4 w/w% of fine grind beta (1,3) glucan.

TABLE 4

Photoprotective Effects of 4% Glucan Formulation (assessed via Minolta Meter readings)

| Site Number | Product Treatment (refer to Table for UV exposure) | Erythema 24 Hours |
| --- | --- | --- |
| 1 | no product | 0 |
| 2 | base lotion | 12.6 |
| 3 | base + 4% glucan* - 1 appl. before UV | 11.3 |
| 4 | base + 4% glucan* - 5 day appl. before UV | 4.5 |
| 4A | base + 4% glucan* - 5 day appl. before UV | 7.7 |
| 4B | base + 4% glucan* - 5 day appl. before UV | 12.9 |
| 5 | SPF 15 - 1 appl. before UV | 8.7 |
| 6 | SPF + 4% glucan* - 1 appl. before UV | 7.9 |
| 6A | SPF + 4% glucan* - 1 appl. before UV | 13.1 |
| 6B | SPF + 4% glucan* - 1 appl. before UV | 12.2 |
| 10 | 4% glucan* after exposure | 12.7 |

*4% glucan = glycerine/1,3-butylene glycol composition comprising 4 w/w% of fine grind beta (1,3) glucan.

TABLE 5

Visual Grading of Erythema

| Site Number | Product Treatment | Clinical Assessment of erythema (0,+,1); Total Score |
| --- | --- | --- |
| 1 | no product | 0,0,0,0,0,0,0,0,0,0:0 |
| 2 | base lotion | 1,1,1,1,+,1,+,1,1,1:9 |
| 3 | base + 4% glucan* - 1 appl. before UV | 1,1,+,0,1,1,+,1,1,1:8 |
| 4 | base + 4% glucan* - 5 day appl. before UV | 0,,0,0,0,+,+,1,1,0,0:3 |
| 4A | base + 4% glucan* - 5 day appl. before UV | 1,1,+,+,+,+,0,0,0,+: 4.5 |
| 4B | base + 4% glucan* - 5 day appl. before UV | 1,1,1,1,1,1,1,1,1,1:10 |
| 5 | SPF 15 - 1 appl. before UV | +,+,1,0,1,+,1,1,1,1: 7.5 |
| 6 | SPF + 4% glucan* - 1 appl. before UV | 1,1,0,+,1,+,1,+,1,+:7 |
| 6A | SPF + 4% glucan* - 1 appl. before UV | 1,1,1,1,1,1,1,1,1,1:10 |
| 6B | SPF + 4% glucan* - 1 appl. before UV | 1,1,1,1,1,1,1,1,1,1:10 |
| 10 | 4% glucan* after exposure | 1,1,1,1,1,1,1,1,1,1:10 |

*4% glucan = glycerine/1,3-butylene glycol composition comprising 4 w/w% of fine grind beta (1,3) glucan.

Having described the invention above, various modifications of the techniques, procedures, material, and equipment will be apparent to those in the art. It is intended that all such variations within the scope and spirit of the appended claims be embraced thereby.

I claim:

1. A method for improving the growth and survival of animals comprising:
   administering an effective amount of a nutritional supplement to an animal, said nutritional supplement comprising a water-insoluble yeast cell wall extract comprising purified beta (1,3) glucan having a particle size of about 1.0 micron or less.

2. The method of claim 1, wherein said effective amount is from about 0.20 mg to about 1.0 mg of said supplement per 1.0 kg of body weight.

3. The method of claim 1, wherein said administration is oral.

4. The method of claim 1, wherein said animal is a domestic farm animal.

5. The method of claim 1, wherein said animal is a fish.

6. The method of claim 1, wherein said animal is a crustacean.

7. The method of claim 1, wherein said animal is a bird.

8. The method of claim 1, wherein said animal is a human.

9. The method of claim 1, wherein said particle size is about 0.20 microns or less.

10. The method of claim 9, wherein said effective amount is from about 0.20 mg to about 1.0 mg of said supplement per 1.0 kg of body weight.

11. The method of claim 1 wherein said administration is parenteral.

12. The method of claim 1 wherein said animal is a chicken.

13. The method of claim 11 wherein said effective amount is from about 0.001 mg to 0.3 mg per gram of body weight.

* * * * *